United States Patent
Drescher et al.

(10) Patent No.: US 9,903,781 B2
(45) Date of Patent: Feb. 27, 2018

(54) MATERIAL TESTING APPARATUS AND METHOD

(71) Applicant: United Technologies Corporation, Farmington, CT (US)

(72) Inventors: Joseph D. Drescher, Middletown, CT (US); William J. Brindley, Hebron, CT (US)

(73) Assignee: United Technologies Corporation, Farmington, CT (US)

( * ) Notice: Subject to any disclaimer, the term of this patent is extended or adjusted under 35 U.S.C. 154(b) by 0 days.

(21) Appl. No.: 15/128,022

(22) PCT Filed: Mar. 18, 2015

(86) PCT No.: PCT/US2015/021222
§ 371 (c)(1),
(2) Date: Sep. 21, 2016

(87) PCT Pub. No.: WO2015/148208
PCT Pub. Date: Oct. 1, 2015

(65) Prior Publication Data
US 2017/0097280 A1    Apr. 6, 2017

Related U.S. Application Data

(60) Provisional application No. 61/971,741, filed on Mar. 28, 2014.

(51) Int. Cl.
*G01N 3/08* (2006.01)
*G01M 3/08* (2006.01)
(Continued)

(52) U.S. Cl.
CPC .............. *G01M 3/08* (2013.01); *B06B 1/06* (2013.01); *B33Y 50/00* (2014.12); *G01B 7/14* (2013.01);
(Continued)

(58) Field of Classification Search
CPC .. G01M 7/22; B33Y 50/00; G01B 7/14; G01J 5/48; G01N 3/02; G01N 3/32
(Continued)

(56) References Cited

U.S. PATENT DOCUMENTS 4,265,120 A    5/1981  Morris et al.
4,896,339 A    1/1990  Fukumoto
(Continued)

FOREIGN PATENT DOCUMENTS

DE    102007032064 A1    1/2009
EP         1654771 B1     3/2010
(Continued)

OTHER PUBLICATIONS

Slotwinski, John A., "Materials Standards for Additive Manufacturing" from PDES, Inc. Workshop, Engineering Laboratory, National Institute of Standards and Technology, Mar. 14, 2013, www.nist.gov/el/msid/infotest/upload/slotwinski-NIST-AM-Materials, 22 pages.
(Continued)

*Primary Examiner* — Harshad R Patel
*Assistant Examiner* — Octavia Hollington
(74) *Attorney, Agent, or Firm* — Kinney & Lange, P.A.

(57) ABSTRACT

A testing apparatus may include a stand having an aperture and a platform adjacent to the aperture, a clamp adjacent to the platform and configured to hold a coupon, and an actuator within the aperture. The actuator is configured to impart a first force on the platform and the coupon at a specified frequency. The testing apparatus may also include a displacement sensor adjacent to the stand and configured to measure a displacement of the coupon and circuitry connected to the actuator and the displacement sensor with the circuitry configured to collect data from the actuator and the displacement sensor.

21 Claims, 4 Drawing Sheets (51) Int. Cl.
*G01J 5/48* (2006.01)
*G01B 7/14* (2006.01)
*G01N 3/32* (2006.01)
*G01N 3/02* (2006.01)
*B06B 1/06* (2006.01)
*B33Y 50/00* (2015.01)
*G01J 5/00* (2006.01)

(52) U.S. Cl.
CPC ............... *G01J 5/48* (2013.01); *G01N 3/02* (2013.01); *G01N 3/32* (2013.01); *G01J 2005/0077* (2013.01)

(58) Field of Classification Search
USPC ........................................................ 73/788
See application file for complete search history.

(56) References Cited

U.S. PATENT DOCUMENTS

| | | | | |
|---|---|---|---|---|
| 6,247,355 | B1* | 6/2001 | Suresh | G01N 3/42 73/82 |
| 6,715,336 | B1 | 4/2004 | Xu | |
| 6,880,379 | B2 | 4/2005 | Hedberg et al. | |
| 7,987,718 | B2 | 8/2011 | Huber et al. | |
| 8,030,807 | B2 | 10/2011 | Gieras et al. | |
| 8,132,447 | B2* | 3/2012 | Wu | G01N 3/08 73/796 |
| 9,063,048 | B2* | 6/2015 | Koshimizu | G01N 3/42 |
| 2003/0037619 | A1 | 2/2003 | Hage | |
| 2007/0107531 | A1 | 5/2007 | Munz et al. | |
| 2010/0229637 | A1 | 9/2010 | Konaka et al. | |
| 2013/0174666 | A1 | 7/2013 | Hadj Henni et al. | |
| 2016/0231210 | A1* | 8/2016 | Ganser | G01N 3/36 |

FOREIGN PATENT DOCUMENTS

| | | |
|---|---|---|
| EP | 2420815 A2 | 2/2012 |
| JP | 5158887 B2 | 3/2013 |
| WO | WO2013022264 A1 | 2/2013 |

OTHER PUBLICATIONS

Long, Rob, "New ASTM Standard Addresses Additive Manufacturing", from Accutek's Blog, http://www.accuttektesting.com/about-us/blog/new-astm-standard-addresses-additive-manufacturing/, visited Feb. 28, 2014, 14 pages.

"Fundamental Measurement Science for Additive Processes Project", from Engineering Laboratory, National Institute of Standards and Technology, http://www.nist.gov/el/isd/sbm/fundmeasursci.cfm, visited Feb. 28, 2014, 5 pages.

"Materials Standards for Additive Manufacturing", from Engineering Laboratory, National Institute of Standards and Technology, http://www.nist.gov/el/isd/sbm/matstandaddmanu.cfm, visited Feb. 28, 2014, 4 pages.

International Search Report and Written Opinion, Application No. PCT/US2015/021222 dated Jun. 12, 2015, 12 pages.

Extended European Search Report for EP Application No. 15767819.4, dated Nov. 13, 2017, 8 pages.

* cited by examiner

MATERIAL TESTING APPARATUS AND METHOD

BACKGROUND

The present invention relates to a testing apparatus and, more particularly, to a testing apparatus and testing method suitable for use with materials made during additive manufacturing processes.

In manufacturing processes, especially in additive manufacturing, it is necessary to know the constructed material's properties and ascertain whether the material contains defects. Monitoring of the material during construction is extremely complicated and expensive, so it is usually more desirable to test the material after construction. To do this, a work piece (often called a test piece or test coupon) may be constructed along with the designed material. The test piece is then subjected to various tests to determine the material's properties and/or defects.

SUMMARY

A testing apparatus can include a stand having an aperture and a platform adjacent to the aperture, a clamp adjacent to the platform and configured to hold a coupon, and an actuator within the aperture. The actuator is configured to impart a first force on the platform and the coupon at a specified frequency. The testing apparatus can also include a displacement sensor adjacent to the stand and configured to measure a displacement of the coupon. Finally, the testing apparatus can include circuitry connected to the actuator and the displacement sensor with the circuitry configured to collect data from the actuator and the displacement sensor.

Another embodiment of a testing apparatus can include a stand having a platform, a clamp attached to the stand and configured to hold a fixed end of a test piece, a displacement sensor adjacent to the stand and configured to measure a displacement of a free end of the test piece, an actuator adjacent to the free end and configured to impart a vibration force on the free end at a specified frequency, a load cell adjacent to the free end and configured to measure a static force on the free end, and circuitry connected to the displacement sensor, actuator, and load cell with the circuitry configured to collect data from the displacement sensor, actuator, and load cell.

A method of testing a work piece can include placing the work piece in a testing apparatus. The testing apparatus can include a stand having a platform, a clamp adjacent to the platform and configured to hold the work piece, an actuator adjacent to the work piece, a displacement sensor configured to measure a displacement of the work piece, and circuitry connected to the actuator and the displacement sensor and configured to collect data. The method can also include imparting a force on the work piece and collecting data produced by imparting the force and measuring the displacement of the work piece by the displacement sensor.

While the above-identified figures set forth embodiments of the present disclosure, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale, and applications and embodiments of the present invention may include features and components not specifically shown in the drawings.

DETAILED DESCRIPTION

The disclosed testing apparatus and method allows for the performance of various tests to determine the mechanical properties of a material of a work piece (also called a coupon or test piece) and to discover if the work piece's material has any defects. The properties and defects determined by the tests can be determined from other tests (performed in a different manner and using a different machine), but because the tests performed by the testing apparatus can determine these properties and defects multiple ways (through different tests), the accuracy and certainty of the discovered properties and defects are substantially increased. The testing apparatus and method can be used/performed quickly and easily to allow for results to be obtained in many environments. The testing apparatus is light and compact to allow easy transport while still producing quick and accurate results. The data collected by the testing apparatus can provide insight into the properties and defects of a designed element, which is constructed under the same conditions as the work piece so as to exhibit the same or similar material characteristics. By knowing the material characteristics of the designed element, designers and builders can determine if the designed element meets desired specifications and/or adjust the material's composition and manufacturing process to make a material that better suits the desired specifications.

Figure 1:
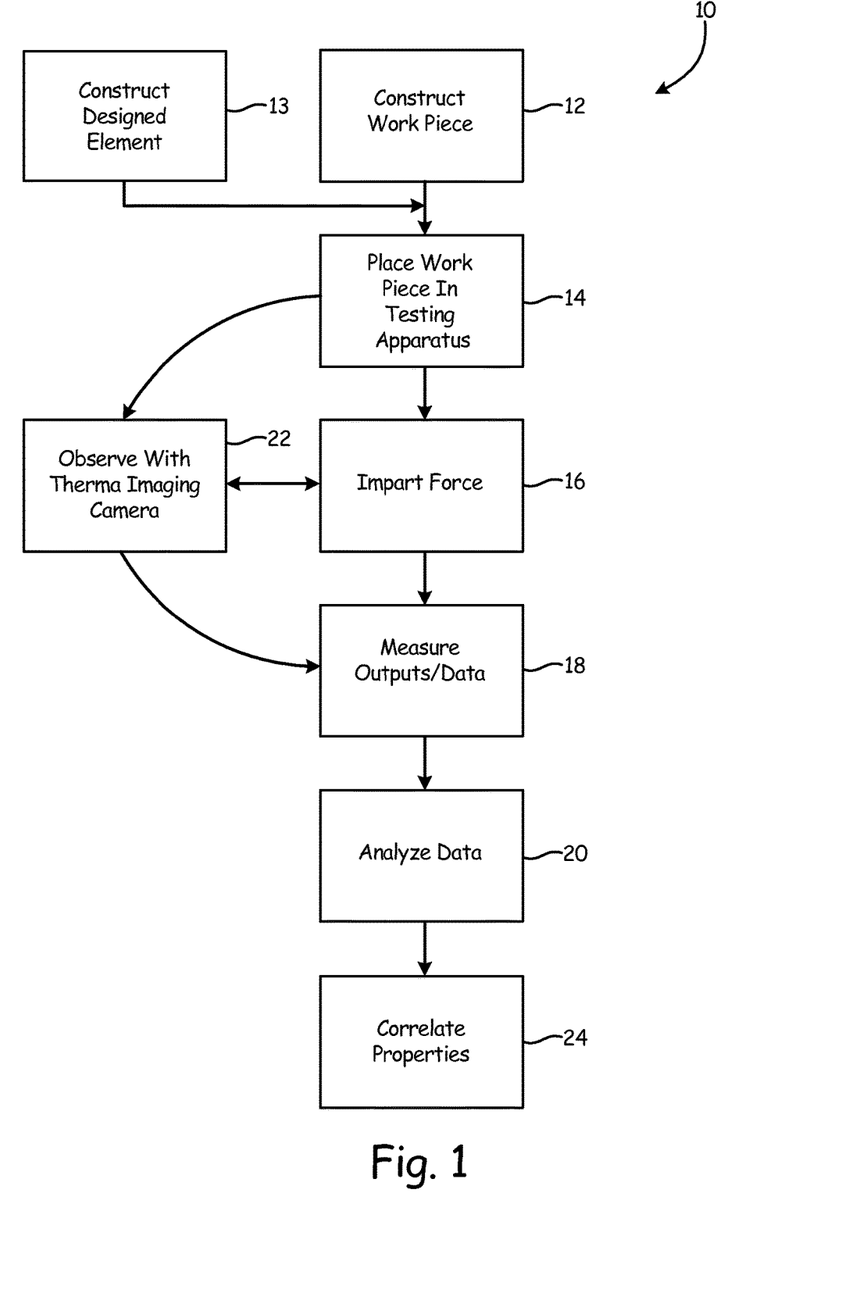
FIG. 1 is a flow chart of an embodiment of a manufacturing and testing process.

FIG. 1 is a flow chart of an embodiment of a manufacturing and testing process of a work piece. Manufacturing and testing process ("process") 10 includes construction of the work piece (step 12), construction of designed element (step 13) placing work piece in the testing apparatus (step 14), imparting force on the work piece (step 16), measuring and collecting outputs/data (step 18), analyzing the data (step 20), and correlating the work piece properties to the designed element properties (step 24). The work piece can also be observed with a thermal imaging camera (step 22) when the work piece is in the testing apparatus. The manufacturing and testing process during actual performance can include more steps than those set out in process 10, for process 10 only highlights some possible steps. Furthermore, in alternate embodiments, certain illustrated steps can be omitted.

First, construction of the work piece (step 12) is performed. The work piece is usually constructed using the same materials and at the same time or very close in time as the construction of designed element (step 13), whose properties and integrity (whether or not the designed element/material has any defects) are desired to be known. This ensures that the work piece has a similar material composition/makeup as the designed element. The work piece and designed element may be of any desired material, but are usually a metal or metallic composite constructed through an additive manufacturing process. The work piece may also have any configuration (size and shape) that allows for testing (discussed in further detail below). The intent of the work piece is to be a representative of the designed element so that the materials of the work piece exhibit the same properties and potential defects of the designed element, allowing insight into the characteristics of the design element without the need to test, and potentially destroy during testing, the design element.

After construction of the work piece (step 12) and construction of the designed element (step 13), the work piece is placed in the testing apparatus (step 14). The testing apparatus will be discussed in further detail below, but the testing apparatus can be near the facility where construction of the work piece (step 12) and construction of the designed element (step 14) take place or remote to the facility. Additionally, as mentioned above, the testing apparatus is portable and can be transported when convenient.

Once the work piece is placed in the testing apparatus (step 14), a test begins by imparting force on the work piece (step 16). The testing apparatus is able to conduct a number of different tests to determine various properties and defects of the work piece's material. Some of the various tests able to be performed by the testing apparatus are discussed in further detail below. The force can be imparted at a number of different locations and at different intervals/frequencies, depending on the particular test being performed.

While force is being imparted on the work piece (step 16), the work piece can also be observed by a thermal imaging camera (step 22). The thermal imaging camera can provide data regarding potential defects in the materials of the work piece that other devices cannot detect. The use of the thermal imaging camera will be discussed further below.

During and after force is imparted on the work piece (step 16), process 10 includes measuring and collecting outputs/data (step 18). This can be done by monitoring the force imparted on the work piece, the images captured by the thermal imaging camera, and the displacement of the work piece measured by a displacement sensor. Other outputs/data can also be measured and collected during and after each test by various sensors within testing apparatus.

Figure 4A:
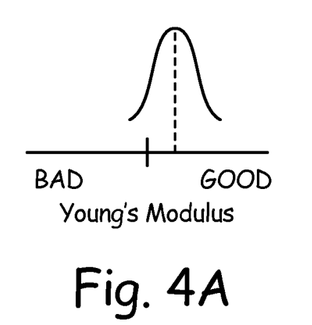
FIGS. 4A-4F are curves representing various properties and defects determined by the testing process.
Figure 4B:
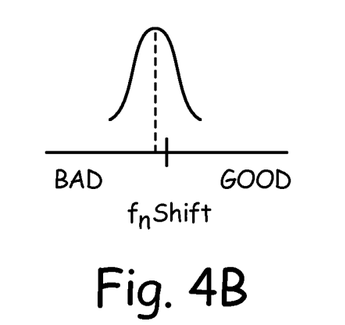
Figure 4C:
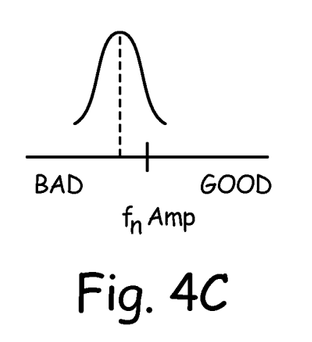
Figure 4D:
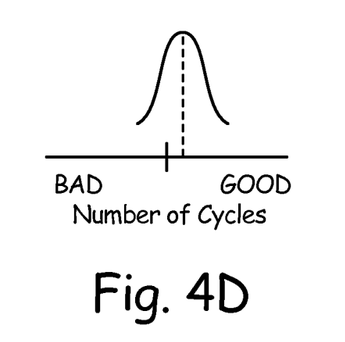
Figure 4E:
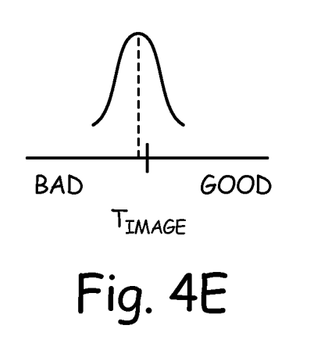
Figure 4F:
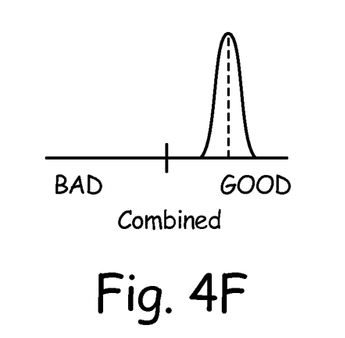

Then, an analysis of the data (step 20) is performed to determine various properties and defects of the materials of the work piece. This data can be plotted onto various curves to represent uncertainty as a distribution of the value of various properties and defects (FIGS. 4A-4E) and combined to represent a more accurate determination of the material's characteristics (FIG. 4F). The analysis may show that the work piece (and hence the designed element) exhibits the desired design characteristics sufficient for the designed element's intended use. The analysis may also show defects in the material of the work piece that makes the material unsatisfactory for its intended use. The analysis may also lead to the identification and quantification of high priority process inputs/parameters, establish limits for each of these process inputs, and establish methods for control of these inputs during the construction of the work piece 12 and the designed element.

Finally, the information and properties collected through the testing of the work piece is correlated to the design element properties (step 24). Because the work piece is constructed under the same or similar conditions to that of the designed element, the properties and defects of the work piece should be the same or very similar to the properties and defects of the designed element. With this information, designers and builders can determine if the designed element meets desired specifications and/or adjust the material's composition and manufacturing process to make a material that better suits the desired specifications. As an example, results of the tests and associated, established limits may determine whether or not additional processing operations are required to bring properties of the designed element within specification. Such an operation may include Hot Isostatic Pressing (HIP). Additionally, material quality across multiple builds can be more closely monitored by performing multiple tests on multiple work pieces.

Figure 2:
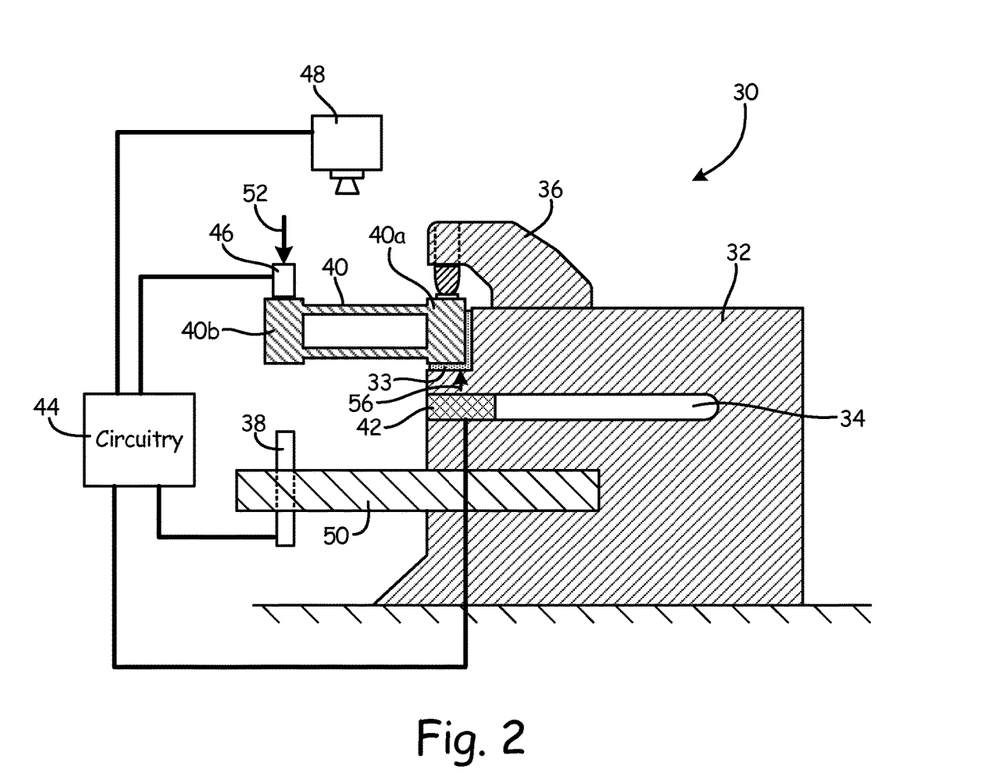
FIG. 2 is a cross-sectional elevation view of an embodiment of a testing apparatus.

FIG. 2 is a cross-sectional elevation view of one embodiment of testing apparatus 30. Testing apparatus 30 includes stand 32, platform 33, aperture 34, clamp 36, displacement sensor 38, work piece 40 (which includes fixed end 40a and free end 40b), actuator 42, circuitry 44, load cell 46, and thermal imaging camera 48. Displacement sensor 38 can be attached to stand 32 or otherwise held in place by sensor arm 50. Static force 52 can be imparted/applied to work piece 40 near load cell 46 and vibration force 56 can be imparted to work piece 40 by actuator 42.

The main component that provides structural support for testing apparatus 30 is stand 32, which is attached to ground so as to remain stable and immovable during the performance of a test. Stand 32 can be made from one or a number of materials, including plastic or metal (such as aluminum), that are strong enough to provide support to various components of testing apparatus 30. Additionally, stand 32 must be able to withstand static and dynamic loads/forces (such as static force 52 and/or vibration force 56) that may transfer to stand 32 after being imparted on work piece 40. Stand 32 can be one continuous piece or a number of pieces that are configured to efficiently, consistently, and accurately transfer force from actuator 42 to work piece 40 without damage or failure. Stand 32 can be designed to house other components within it, such as various sensors, replacement components, or other devices.

Adjacent to or within stand 32 is platform 33, which can be an indentation in stand 32 that holds one end of work piece 40. Platform 33 can also be another configuration, such as a flat surface that is smooth or coarse. Platform 33 can also extend the entire width of stand 32 (into and out of the page in FIG. 2) or can be only wide enough to fit a narrower end of work piece 40. The material of stand 32 around platform 33 can be the same or a different material than that of the rest of stand 32. Additionally, platform 33 can have wedges or other configurations to help secure work piece 40. Platform 33 should be configured to efficiently, consistently, and accurately transfer vibration force 56 from actuator 42 to work piece 40 without damaging or failing while holding work piece 40 securely.

Adjacent to platform 33 and stand 32 is clamp 36, which is configured to hold work piece 40 securely in place on platform 33 of stand 32. Clamp 36 can be a fixed structure (fixed to stand 32) and fastener, a spring-loaded configuration, or another suitable mechanism that secures work piece 40 to platform 33 and stand 32. Clamp 36 ensures that work piece 40 remains in place on platform 33 during the performance of a test.

Within stand 32 is aperture 34, which can extend horizontally into stand 32 to provide an area in which actuator 42 is housed. Aperture 34 can extend substantially into stand 32 (as shown in FIG. 2) or can be just shallow enough to sufficiently house any sized of actuator 42. Additionally, aperture 34 can extend the entire width of stand 32 (into and out of the page in FIG. 2) or can be only wide enough to fit a narrower configuration of actuator 42. Aperture 34 should be configured so as to efficiently, consistently, and accurately transfer vibration force 56 from actuator 42 to work piece 40. Aperture 34 can also house other components of testing apparatus 30, such as a portion of circuitry 44 and/or other sensors. The material of stand 32 adjacent to aperture 34 can be the same or a different material than that of the rest of stand 32.

Within aperture 34 is actuator 42, which can be any type of actuator, such as a mechanical or electrical actuator, that can impart vibration force 56 or a pulse force (one static force for a set duration; usually a short duration) onto work piece 40. Additionally, actuator 42 can be a piezoelectric material. A piezoelectric material is a material that shows a marked piezoelectric effect such that the introduction of an electrical charge results in the generation of an applied mechanical force. The piezoelectric material can be a number of suitable substances, such as lead zirconate titanate (PZT) or similar substances and should be configured to, when given an electric charge, impart vibration force 56 at a desired frequency onto work piece 40 or a pulse force onto work piece 40.

Vibration force 56 imparted on work piece 40 by actuator 42 should be consistent and measurable by circuitry 44 or other sensors so as to later allow for analysis of the response of work piece 40 to vibration force 56 imparted by actuator 42. Other embodiments can have another component or components in place of actuator 42 that can impart a consistent and measurable force on work piece 40. Actuator 42 should be able to withstand multiple tests without damage or failure. Additionally, in further embodiments, actuator 42 can be positioned at other locations of testing apparatus 30.

Secured to platform 33 of stand 32 by clamp 36 is work piece 40 (also called a coupon or test piece). As mentioned above, work piece 40 should be a representative piece of the material of a designed element so as to exhibit similar properties and defects. Work piece 40 may be any size and shape that will accurately and consistently exhibit the characteristics of the material of the designed element, such as a cylinder or single cantilever beam configuration. In testing apparatus 30, work piece 40 has a double cantilever beam (also known as a parallel flexure) configuration to allow for the performance of a variety of different tests on work piece 40 that may not otherwise be able to be performed with a different configuration of work piece 40. Work piece 40 should be large enough to ensure that the surface finish effects of work piece 40 are negligible, but no larger than necessary due to the expense of the material and area available during construction of work piece 40 and the designed element. The width (into and out of the page in FIG. 2) can be varied, from a fraction of a few millimeters to a centimeter or more, depending on the material being tested, the test being performed, and the characteristics of the material of work piece 40. Work piece 40 allows for end conditions that provide for pure translation such that the location of force and measurement of displacement is less critical. Work piece 40 of testing apparatus 30 has fixed end 40a held by platform 33 of stand 32 and clamp 36. Extending away from fixed end 40a is free end 40b adjacent to load cell 46 and displacement sensor 38. Between fixed end 40a and free end 40b is the double cantilever beam configuration. During various tests, work piece 40 can momentarily or permanently deflect or deform (elastic or plastic deformation) due to vibration force 56 imparted on work piece 40 by actuator 42 or another force, such as force 52. Work piece 40 can also fail due to fatigue, cracking, etc.

Adjacent to stand 32 and work piece 40 is displacement sensor 38, which can be attached to stand 32 by sensor arm 50. Displacement sensor 38 measures the displacement of work piece 40 and in FIG. 2 the displacement of free end 40b of work piece 40. Displacement sensor 38 can be configured to measure the displacement of work piece 40 in any direction. Displacement sensor 38 can be a linear variable differential transformer or another sensor that is able to measure very small displacements, such as a capacitance, inductance, confocal, or other optical indicator. The measurements by displacement sensor 38 are then conveyed to circuitry 44 (or another device) to allow for analysis of the response of work piece 40 to vibration force 56 imparted on work piece 40 by actuator 42 or another force imparting component. While displacement sensor 38 of testing apparatus 30 is positioned directly below free end 40b of work piece 40, displacement sensor 38 can measure displacement of work piece 40 from another location. Displacement sensor 38 can measure displacement without contacting work piece 40 or while also in contact with work piece 40.

Sensor arm 50 holds displacement sensor 38 securely in place relative to stand 32. Sensor arm 50 can be attached to stand 32 by various means, such as a fastener or another suitable mechanism, or can be attached to ground. Sensor arm 50 should be sufficiently strong to prevent movement of displacement sensor 38 to ensure that the measurements taken by displacement sensor 38 are accurate and consistent.

Load cell 46 is positioned at the free end of work piece 40 and is configured to measure force 52 or another force applied/imparted on free end 40b of work piece 40 during various tests, such as a static load/force test. Load cell 46 can be any device or sensor that measures the load imparted/applied onto work piece 40. Force 52 would be applied to one side of load cell 46 and transferred through load cell 46 (at this point force 52 applied/imparted would be measured by load cell 46) to work piece 40. The measurements of force 52 by load cell 46 would then be conveyed to circuitry 44 (or another device) to allow for analysis of the response to force 52 by work piece 40. While testing apparatus 30 of FIG. 2 shows load cell 46 adjacent to free end 40b of work piece 40, load cell 46 may be positioned at any location adjacent to work piece 40 where a force is desired to be applied to work piece 40 and measured by load cell 46.

During the static load/force test (discussed further below), force 52, load cell 46, free end 40b, and displacement sensor 38 can be aligned such that force 52 causes pure translation of free end 40b of work piece 40 to allow for an easier and more accurate determination of the properties of the material of work piece 40. For other tests, the configuration of these components may be different.

Testing apparatus 30 can also include thermal imaging camera 48, which can be positioned to observe work piece 40 before, during, and after a test is performed. Thermal imaging camera 48 can be an infrared camera or other imaging device that is able to observe and detect defects in the material of work piece 40. Thermal imaging camera can detect any defects in the material of work piece 40 through the dissipation of energy as heat or other changes in work piece 40. Thermal imaging camera 48 can be connected to circuitry 44 (or another device) so that the images and other information collected by thermal imaging camera 48 are conveyed to circuitry 44 to connect the information collected by thermal imaging camera 48 to the other data collected and allow for analysis of the response by the material of work piece 40 to a force. While thermal imaging camera 48 of testing apparatus 30 in FIG. 2 is shown observing work piece 40 from the top, thermal imaging camera 48 can be positioned to observe work piece 40 from another location/orientation.

Connected to displacement sensor 38, actuator 42, load cell 46, and thermal imaging camera 48 (and possibly other components not shown in FIG. 2) is circuitry 44. Circuitry 44 can include wires that connect to those components or may be wirelessly connected to the components of test apparatus 30. Circuitry 44 is configured to accept data/outputs from displacement sensor 38 in the form of displacement measurements, from actuator 42 and load cell 46 in the form of forces imparted (measurement is likely of an electrical charge created by actuator 42 or load cell 46 that is proportional to the force imparted), and from thermal imaging camera 48 in the form of images or other observable data/outputs. Circuitry 44 can also accept data/outputs from other components of testing apparatus 30 to monitor other variables before, during, and after the performance of a test. Circuitry 44 can be configured to compile the data/outputs and organize it into analyzable readouts or other viewable compilations, such as graphs and curves. Circuitry 44 can also manipulate the data/outputs to calculate various mechanical properties and defects. Circuitry 44 can include a processor or be connected to a computer (not shown) that manipulates the data/outputs similarly or more extensively to arrive at values and graphs that are helpful to those designing the material of work piece 40 and the designed element.

As mentioned above, testing apparatus 30 is useful in that in can be used to perform a wide variety of tests on work piece 40 to determine various properties and defects of the material of work piece 40. The properties and defects determined by testing apparatus 30 can be determined from other tests (performed in a different manner and using a different machine), but because the tests performed by testing apparatus 30 can determine these properties and defects multiple ways (through different tests), the accuracy and certainty of the discovered properties and defects are substantially increased. A number of these tests are described below, but testing apparatus 30 is able to perform other tests.

One test able to be performed by testing apparatus 30 is a static load/force test. In this test, a load/force (such as static force 52) is imparted on work piece 40 near load cell 46. The force applied can be a static force applied for a particular extended duration or may be a pulse force applied for only a short time. During the static load/force test, static force 52 is measured by load cell 46 and conveyed to circuitry 44, while the displacement of work piece 40 is measured by displacement sensor 38 and conveyed to circuitry 44. With this data, certain material properties and defects may be determined, such as the material's Young's modulus, yield strength, ultimate strength, and others. Depending on the size of static force 52 applied and the amount of displacement/deformation of work piece 40, the static load/force test can be a destructive or nondestructive test of work piece 40. Static force 52 can be applied to other areas of work piece 40 to determine other material properties and defects. The data collected by the static load/force test can be analyzed and/or plotted on graphs/curves (FIGS. 4A-4F) to determine if the properties and defects of the material of work piece 40 (and the corresponding designed element) meets the desired properties and defects, or the information collected can be compared to other materials.

Another test able to be performed by testing apparatus 30 is a vibration spectrum analysis. In this test, a load/force (such as vibration force 56) is imparted on work piece 40 by actuator 42. Vibration force 56 imparted can be a pulse force imparted for only a short time or a force applied at a particular frequency (the force is repeatedly applied for a consistent or varying duration of time). During the vibration spectrum analysis, vibration force 56 is measured by circuitry 44. This data is then conveyed to circuitry 44. The displacement of work piece 40 caused by vibration force 56 imparted by actuator 42 is measured by displacement sensor 38 and conveyed to circuitry 44.

Vibration force 56 may be imparted at a variety of frequencies depending on the material of work piece 40 and the properties desired to be determined. With the vibration spectrum analysis, the rate of application of the force and amplitude of the force would be varied to observe a frequency shift, which is the change in vibration of work piece 40, damping, which is the change in the amplitude of vibration of work piece 40, and other responses to the force by work piece 40. This test can be performed quickly because vibration force 56 does not need to be imparted onto work piece 40 for an extended duration of time. The vibration spectrum analysis does not have to be a destructive test that causes plastic deformation of work piece 40. The data/outputs collected by this test can allow for the determination of certain properties, such as elastic modulus, porosity, and others, and can show any defects in the material of work piece 40. The data could be further analyzed and/or plotted (FIGS. 4A-4F) to determine variations in resonance amplitude and frequency on the response spectrum (damping) and to determine if the properties and defects of the material of work piece 40 (and the corresponding designed element) meet the desired material characteristics. Specifically, FIG. 4B is a curve of the frequency shift and FIG. 4C is a curve of the frequency amplitude as determined through performance of the vibration spectrum analysis.

Another test able to be performed by testing apparatus 30 is a high cycle fatigue analysis. This test is similar to the vibration spectrum analysis. A load/force (such as vibration force 56) is imparted on work piece 40 by actuator 42. Unlike the vibration spectrum analysis, vibration force 56 imparted in the high cycle fatigue analysis is usually imparted at a particular, consistent frequency for an extended duration. During the high cycle fatigue analysis, vibration force 56 is measured and collected by circuitry 44 and the displacement of work piece 40 caused by vibration force 56 imparted by actuator 42 is measured by displacement sensor 38 and conveyed to circuitry 44.

In the high cycle fatigue test, vibration force 56 can be imparted at a variety of frequencies depending on the material of work piece 40 and the properties desired to be determined With this test, the frequency of vibration force 56 is usually consistent over an extended duration of time in an attempt to observe how the material of work piece 40 responses when work piece 40 is fatigued and/or close to failure. This response is collected by the various sensors of testing apparatus 30 and conveyed to circuitry 44, which then can analyze the data and determine certain properties and defects of the material of work piece 40. The data/outputs collected by this test can allow for the determination of certain properties and defects and could be further analyzed and/or plotted to determine such things as the number of cycles it took the material of work piece 40 to fail (FIGS. 4A-4F; specifically, FIG. 4D). This information could be compared to information gathered from other materials or to the desired properties and defects to determine if the material of work piece 40 (and the corresponding designed element) meets the desired material characteristics.

Another test able to be performed by testing apparatus 30 is a sonic thermal imaging analysis. In this test, a load/force (such as vibration force 56) is imparted on work piece 40 by actuator 42 or a similar device at a particular frequency, such as the natural resonance frequency of the material of work piece 40. Therefore, this test could occur simultaneously.

The response by work piece 40 to vibration force 56 is observed with thermal imaging camera 48. Like the other tests, vibration force 56 is measured and collected by circuitry 44 and the displacement of work piece 40 caused by vibration force 56 imparted by actuator 42 or a similar device is measured by displacement sensor 38 and conveyed to circuitry 44. Some properties and defects of the material of work piece 40 can only be attainable through observation of the energy dissipation. By observing with thermal imaging camera 48 the temperature of the material at various locations, these properties and defects can be determined. The data/outputs collected and analyzed by this test could be plotted to form a curve of the temperature of the material of work piece 40 (FIG. 4E). The information obtained by the sonic thermal imaging analysis could be compared to information gathered from other materials or to the desired properties and defects to determine if the material of work piece 40 (and the corresponding designed element) meets the desired properties and defects (FIGS. 4A-4F).

If useful, all of the data, properties, and potential defects could be compared, analyzed, and plotted to determine if the overall composition of the material of work piece 40 meets the desired properties and defects (FIG. 4F). This is particularly useful for materials made during an additive manufacturing process. This information could be compared to other materials made during additive manufacturing processes that have undergone the same tests to form a larger body of data that allows for quick and easy determinations of whether the material meets desired specification and is sufficient for its intended purpose. As mentioned above, other tests can be performed by testing apparatus 30 to determine material properties and defects. Additionally, the tests can be performed on a test piece that has a different size and shape than that of work piece 40 and on a testing apparatus that has a different configuration than that of testing apparatus 30, such as the testing apparatus of FIG. 3.

Figure 3:
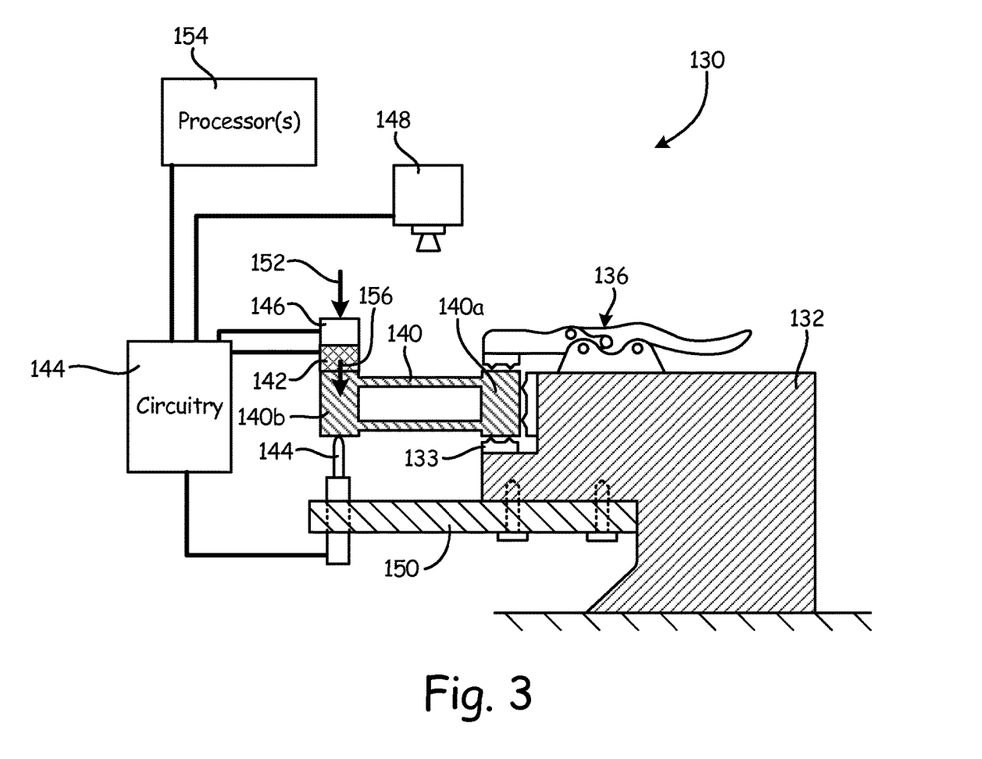
FIG. 3 is a cross-sectional elevation view of another embodiment of a testing apparatus.

FIG. 3 is a cross-sectional elevation view of another embodiment of a testing apparatus. Testing apparatus 130 includes stand 132, platform 133, clamp 136, displacement sensor 138, work piece 140 (which includes fixed end 40a and free end 40b), actuator 142, circuitry 144, load cell 146, thermal imaging camera 148. Displacement sensor 138 can be attached to stand 132 or otherwise held in place by sensor arm 150. Circuitry 144 may be connected to processor 154. Static force 152 and/or vibration force 156 may be imparted/applied to work piece 140 near load cell 146 and actuator 142.

Testing apparatus 130 is similar to testing apparatus 30 of FIG. 2. Stand 132 provides structural support to the other components of testing apparatus 130. Adjacent to or within stand 132 is platform 133, which helps secure one end of work piece 140 and can include wedges or other devices that help hold work piece 140. Adjacent to stand 132 and platform 133 is clamp 136, which is also adjacent to and helps secure one end of work piece 140. Work piece 140 (also called a coupon or test piece) is held at one end by platform 133 and clamp 136. Work piece 140 can be a number of different materials, have a variety of sizes and shapes, and be configured to extend horizontally away from stand 132. Thermal imaging camera 148 can be positioned to observe work piece 140 before, during, and after a test is performed.

Positioned adjacent to free end 140b of work piece 140 is actuator 142, which can perform the same functions as actuator 42 of FIG. 2, except that actuator 142 is not positioned adjacent to stand 132. While actuator 142 is positioned at free end 140b of work piece 140 in FIG. 3, actuator 142 may be located anywhere along work piece 140 that allows for actuator 142 to efficiently, consistently, and accurately impart force (such as vibration force 156) onto work piece 140. Adjacent to free end 140b of work piece 140 and actuator 142 is load cell 146, which can be configured to measure static force 152 imparted on work piece 140. Also adjacent to the free end of work piece 140 is displacement sensor 138, which may or may not be in contract with work piece 140. Displacement sensor 138 is securely held by sensor arm 150, which can be fastened to stand 132 or otherwise supported to hold displacement sensor 138. The weight of actuator 142 and load cell 146 should not be so much that it causes significant stress, strain, and deformation of work piece 140 before a test is performed.

Connected to displacement sensor 138, actuator 142, load cell 146, thermal imaging camera 148, and possibly other components of testing apparatus 130 is circuitry 144. Circuitry 144 can include wires or can be wirelessly connected to those components. Circuitry 144 can be configured to compile data/outputs conveyed to circuitry 144 and organize the data/outputs into analyzable readouts or other viewable compilations. Circuitry 144 can also be able to manipulate the data/outputs to calculate various mechanical properties and defects, as well as generating graphs and curves.

Circuitry 144 can include or be connected to processor 154, which can be a computer or connected to a computer that manipulates the data/outputs similarly or more extensively than circuitry 144 to arrive at values and graphs that are helpful to those designing the material of work piece 140 and the designed element.

Testing apparatus 130 can perform a wide variety of tests that may be useful to the determination of properties and defects of the material of work piece 140, including the tests discussed with regard to testing apparatus 30 of FIG. 2. As with the tests and testing apparatus 30 described above, testing apparatus 130 allows for analysis of the material of work piece 140 to determine whether the material (which is the same or similar to the material of the designed element) meets desired specification and is sufficient for its intended purpose.

Discussion of Possible Embodiments

The following are non-exclusive descriptions of possible embodiments of the present invention.

A testing apparatus can include a stand having an aperture and a platform adjacent to the aperture; a clamp adjacent to the platform and configured to hold a coupon; an actuator within the aperture, the actuator configured to impart a first force on the platform and the coupon at a specified frequency; a displacement sensor adjacent to the stand and configured to measure a displacement of the coupon; and circuitry connected to the actuator and the displacement sensor, the circuitry configured to collect data from the actuator and the displacement sensor.

The apparatus of the preceding paragraph can optionally include, additionally and/or alternatively, any one or more of the following features, configurations, and/or additional components:

A free end of the coupon extends horizontally away from the platform to form a parallel cantilever beam and a fixed end of the coupon is held between the clamp and the platform.

A thermal imaging camera focused on the coupon, the thermal imaging camera connected to the circuitry and configured to convey data to the circuitry.

A load cell adjacent to the free end and configured to measure a second force imparted on the free end, the load cell connected to the circuitry and configured to convey data to the circuitry.

The displacement sensor is in contact with the coupon.

The actuator is a piezoelectric material that is configured to impart a first force on the platform and the coupon at a specified frequency in response to an applied electrical charge.

Another embodiment of a testing apparatus can include a stand having a platform; a clamp attached to the stand and configured to hold a fixed end of a test piece; a displacement sensor adjacent to the stand and configured to measure a displacement of a free end of the test piece; an actuator adjacent to the free end and configured to impart a vibration force on the free end at a specified frequency; a load cell adjacent to the free end and configured to measure a static force on the free end; and circuitry connected to the displacement sensor, actuator, and load cell, the circuitry configured to collect data from the displacement sensor, actuator, and load cell.

The apparatus of the preceding paragraph can optionally include, additionally and/or alternatively, any one or more of the following features, configurations, and/or additional components:

A thermal imaging camera focused on the test piece, the thermal imaging camera connected to the circuitry and configured to convey data to the circuitry.

A processor connected to or contained within the circuitry that allows analysis of the data received from the circuitry.

The test piece extends horizontally away from the stand and forms a parallel cantilever.

The actuator is a piezoelectric material configured to impart a vibration force on the free end at a specified frequency in response to an applied electrical charge.

A method of testing a work piece can include placing the work piece in a testing apparatus, the testing apparatus includes a stand having a platform; a clamp adjacent to the platform and configured to hold the work piece; an actuator adjacent to the work piece; a displacement sensor configured to measure a displacement of the work piece; and circuitry connected to the actuator and the displacement sensor and configured to collect data; imparting a force on the work piece; and collecting data produced by imparting the force and measuring the displacement of the work piece by the displacement sensor.

The method of the preceding paragraph can optionally include, additionally and/or alternatively, any one or more of the following steps, features, configurations, and/or additional components:

The work piece is constructed through additive manufacturing.

The work piece is representative of an untested designed element and the data collected is correlated with the untested designed element.

The actuator is a piezoelectric material that is configured to impart force on the work piece in response to an applied electrical charge.

A free end of the work piece extends away from the platform to form a parallel cantilever beam and a fixed end is held by the clamp.

The force is applied to the free end and the displacement sensor measures the displacement of the free end.

The force is applied to the fixed end by the actuator and the displacement sensor measures the displacement of the free end.

The force is applied to the fixed end by the actuator at a desired frequency.

The force vibrates the work piece at a frequency and for a duration that causes high cycle fatigue of the work piece.

An additional step of observing the work piece with a thermal imaging camera before, during, and after the force has been imparted on the work piece.

The work piece at a natural resonance frequency.

An additional step of analyzing the data received by the circuitry to determine material properties and defects of the work piece.

Any relative terms or terms of degree used herein, such as "substantially," "essentially," "generally," "approximately," and the like, should be interpreted in accordance with and subject to any applicable definitions or limits expressly stated herein. In all instances, any relative terms or terms of degree used herein should be interpreted to broadly encompass any relevant disclosed embodiments as well as such ranges or variations as would be understood by a person of ordinary skill in the art in view of the entirety of the present disclosure, such as to encompass ordinary manufacturing tolerance variations, incidental alignment variations, alignment or shape variations induced by thermal, rotational, or vibrational operational conditions, and the like.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A testing apparatus comprising:
a stand having an aperture and a platform adjacent to the aperture;
a clamp adjacent to the platform and configured to hold a coupon with the coupon having a fixed end held between the clamp and the platform and a free end that extends away from the platform;
an actuator within the aperture, the actuator configured to impart a first force on the platform and the coupon at a specified frequency;
a displacement sensor adjacent to the stand and configured to measure a displacement of the coupon; and
circuitry connected to the actuator and the displacement sensor, the circuitry configured to collect data from the actuator and the displacement sensor.

2. The testing apparatus of claim 1, further comprising:
a thermal imaging camera focused on the coupon, the thermal imaging camera connected to the circuitry and configured to convey data to the circuitry.

3. The testing apparatus of claim 1, further comprising:
a load cell adjacent to the free end and configured to measure a second force imparted on the free end, the load cell connected to the circuitry and configured to convey data to the circuitry.

4. The testing apparatus of claim 1, wherein the displacement sensor is in contact with the coupon.

5. The testing apparatus of claim 1, wherein the actuator is a piezoelectric material that is configured to impart a first force on the platform and the coupon at a specified frequency in response to an applied electrical charge.

6. A testing apparatus comprising:
a stand having a platform;
a clamp attached to the stand and configured to hold a fixed end of a test piece;
a displacement sensor adjacent to the stand and configured to measure a displacement of a free end of the test piece;
an actuator adjacent to the free end and configured to impart a vibration force on the free end at a specified frequency;
a load cell adjacent to the free end and configured to measure a static force on the free end; and
circuitry connected to the displacement sensor, actuator, and load cell, the circuitry configured to collect data from the displacement sensor, actuator, and load cell.

7. The testing apparatus of claim 6, further comprising:
a thermal imaging camera focused on the test piece, the thermal imaging camera connected to the circuitry and configured to convey data to the circuitry.

8. The testing apparatus of claim 6, further comprising:
a processor connected to or contained within the circuitry that allows analysis of the data received from the circuitry.

9. The testing apparatus of claim 6, wherein the test piece extends horizontally away from the stand and forms a parallel cantilever.

10. The testing apparatus of claim 6, wherein the actuator is a piezoelectric material configured to impart a vibration force on the free end at a specified frequency in response to an applied electrical charge.

11. A method of testing a work piece, the method comprising:
placing the work piece in a testing apparatus with the work piece having a fixed end and a free end that extends away from the fixed end to form a parallel cantilever beam, the testing apparatus includes:
a stand having a platform;
a clamp adjacent to the platform and configured to hold the fixed end of the work piece;
an actuator adjacent to the free end of the work piece;
a displacement sensor configured to measure a displacement of the work piece; and
circuitry connected to the actuator and the displacement sensor and configured to collect data;
imparting a force on the work piece; and
collecting data produced by imparting the force and measuring the displacement of the work piece by the displacement sensor.

12. The method of claim 11, wherein the work piece is constructed through additive manufacturing.

13. The method of claim 11, wherein the work piece is representative of an untested designed element and the data collected is correlated with the untested designed element.

14. The method of claim 11, wherein the actuator is a piezoelectric material that is configured to impart force on the work piece in response to an applied electrical charge.

15. The method of claim 11, wherein the force is applied to the free end and the displacement sensor measures the displacement of the free end.

16. The method of claim 11, wherein the force is applied to the fixed end by the actuator and the displacement sensor measures the displacement of the free end.

17. The method of claim 16, wherein the force is applied to the fixed end by the actuator at a desired frequency.

18. The method of claim 16, wherein the force vibrates the work piece at a frequency and for a duration that causes high cycle fatigue of the work piece.

19. The method of claim 11, further comprising:
observing the work piece with a thermal imaging camera before, during, and after the force has been imparted on the work piece.

20. The method of claim 19, wherein the force vibrates the work piece at a natural resonance frequency.

21. The method of claim 11, further comprising:
analyzing the data received by the circuitry to determine material properties and defects of the work piece.

* * * * *